United States Patent [19]

Laruelle et al.

[11] Patent Number: 4,661,512

[45] Date of Patent: Apr. 28, 1987

[54] ADAMANTANAMINE DERIVATIVES, PROCESSES FOR THEIR PREPARATION AND DRUGS IN WHICH THEY ARE PRESENT

[75] Inventors: Claude Laruelle, Villeneuve Loubet; Marcel Lepant, Vence; Bernard Raynier, Cagnes, all of France

[73] Assignee: S. A. Panmedica, Carros, France

[21] Appl. No.: 787,995

[22] Filed: Oct. 16, 1985

[30] Foreign Application Priority Data

Oct. 31, 1984 [FR] France .............................. 84 16656

[51] Int. Cl.$^4$ ..................... A61K 31/40; C07D 207/28
[52] U.S. Cl. .................................. 514/423; 548/528; 548/533
[58] Field of Search ................. 548/528, 533; 514/423

[56] References Cited

U.S. PATENT DOCUMENTS

| | | | |
|---|---|---|---|
| 3,152,180 | 10/1964 | Haaf et al. | 564/125 |
| 3,345,399 | 10/1967 | Gerzon et al. | 260/349 X |
| 3,374,244 | 3/1968 | Krimmel | 548/528 |
| 3,478,055 | 11/1969 | Shirakura et al. | 548/533 |
| 3,682,922 | 8/1972 | Klimstra | 548/528 X |
| 3,705,194 | 12/1972 | Scherm et al. | 548/528 X |
| 4,296,110 | 10/1981 | Johnson | 548/533 X |
| 4,448,972 | 5/1984 | Pfeiffer | 548/528 |
| 4,515,715 | 5/1985 | Flegel et al. | 564/153 |

FOREIGN PATENT DOCUMENTS

| | | | |
|---|---|---|---|
| 0081857 | 6/1980 | Japan | 548/533 |
| 0065269 | 4/1983 | Japan | 548/533 |

OTHER PUBLICATIONS

Swallow; Progress Med. Chem., (1971), pp. 119–162.
Schwab, et al.; J. Am. Med. Assoc., 208, (1969), 1168–1170.
Greenstein, et al., "Chemistry of the Amino Acids", vol. 3; pp. 2178, 2189–2194, 2457; John Wiley (N.Y.), [date not available].
Merck Index, 10th ed., listings No. 7685 and 7904 (1983).
Monteiro, Synthesis, (1974), p. 137.
Hardy, Synthesis, (1978), pp. 290–291.

*Primary Examiner*—Joseph Paul Brust
*Attorney, Agent, or Firm*—Browdy and Neimark

[57] ABSTRACT

The present invention relates to new adamantanamine derivatives.

These derivatives correspond to the general formula I:

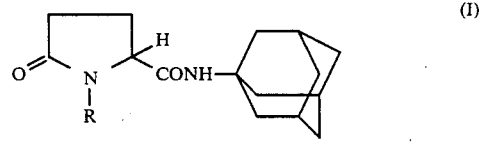

in which: R represents hydrogen or a substituted or unsubstituted, linear or branched alkyl radical containing from 1 to 7 carbon atoms.

Drugs possessing anticonvulsant properties.

12 Claims, No Drawings

ADAMANTANAMINE DERIVATIVES, PROCESSES FOR THEIR PREPARATION AND DRUGS IN WHICH THEY ARE PRESENT

The present invention relates to new adamantanamine derivatives, the process for their preparation and the drugs in which they are present.

Among the bridged hydrocarbon compounds having a pharmacological activity (D. L. SWALLOW, Progr. Med. Chem. (1971) 119), adamantanamine has been studied more particularly for its prophylactic and therapeutic action on influenza virus (U.S. Pat. No. 3,152,180). Effects on the central nervous system have also been demonstrated by R. S. SCHWAB, A. C. ENGLAND, D. C. POSKANZER and R. P. YOUNG (J. Am. Med. Assoc. 108 (1969) 1168) in the treatment of Parkinson's disease.

More recently, European Application No. EP 98.520 has claimed the immunostimulant activities of L-alanyl-D-isoglutaminyladamantylamides.

The prophylactic and therapeutic use of adamantanamine has been known for a long time, but the duration of its action and the appearance of side-effects, such as, for example, insomnia, edema of the lower limbs and neuropsychic, circulatory or trophic disorders, unfortunately restrict its use to individuals who are at high risk from influenza virus.

The aim of the present invention was consequently to provide new adamantanamine derivatives having few side-effects, if any, while at the same time increasing the duration of immunostimulant action of the adamantanamine.

The present invention relates to new adamantanamine derivatives corresponding to the general formula I below:

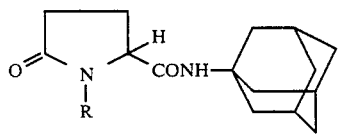

(I)

in which:

R represents hydrogen, a linear or branched alkyl radical containing from 1 to 7 carbon atoms, which is unsubstituted or substituted by an alkoxy, thioalkyl or nitrile group, or an acyl radical of the type:

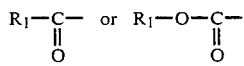

in which:

$R_1$ represents a linear or branched alkyl radical containing from 1 to 7 carbon atoms, a cycloalkyl radical containing 5 to 7 carbon atoms, it being possible for the ring in question to be joined to the carbonyl radical by one or more methylene groups, an aromatic nucleus optionally substituted by substituents such as a halogen atom, the nitro group or $C_1$ to $C_3$ alkyl or alkoxy groups, or a benzyl radical optionally substituted by substituents such as a halogen atom, the nitro group or $C_1$ to $C_3$ alkyl or alkoxy groups.

The present invention also relates to the preparation of the compounds corresponding to the general formula I. The preparation can involve the reaction of the corresponding N-substituted (L)-pyroglutamic acid with adamantanamine in the presence of a coupling agent, for example N,N'-dicyclohexylcarbodiimide or N-ethyl-N'-(dimethylaminopropyl)carbodiimide, in an inert solvent. The preparation can also involve a reactive derivative of the N-substituted (L)-pyroglutamic acid. Among the reactive derivatives which may be employed, it is possible to select the acid halides, the paranitrophenyl and pentachlorophenyl esters and the mixed anhydrides prepared by known reactions using chloroformic acid esters, more generally ethyl chloroformate, or acid chlorides such as pivaloyl chloride.

Solvents which may be employed are halogenoalkanes, ethers, tertiary amines and amides, by themselves or in mixtures, and more precisely pyridine, tetrahydrofuran, acetonitrile, N,N-dimethylformamide, N,N-dimethylacetamide, methylene chloride and chloroform.

In the case where the reactive derivative is an acid halide, an acid acceptor, more commonly pyridine or triethylamine, will advantageously be used.

If R represents hydrogen, the N-substitution of the (L)-pyroglutamic acid is effected starting from (L)-glutamic acid via the N-substituted (L)-glutamic acid, the N-substituted (L)-glutamic anhydride and the dicyclohexylamine salt of the N-substituted (L)-pyroglutamic acid in accordance with the process described by H. Gibian and D. Klieger (Ann. 640, (1961) 145–56).

After the products of the general formula I

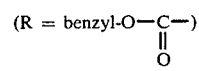

have been obtained, the N-protecting group can be removed by hydrogenolysis, if desired, generally in an aqueous-alcoholic solvent, in the presence of palladium-on-charcoal, to give the product I (R=H).

If R represents an alkyl radical or acyl radical

$R_1$ having the same meaning as previously, the N-substitution of the (L)-pyroglutamic acid is effected by alkylation or acylation of the sodium salt of benzyl (L)-pyroglutamate, followed by catalytic hydrogenation by means of palladium-on-charcoal. The sodium salt is generally prepared in situ via sodium hydride or methylate, in an inert solvent which may be benzene, tetrahydrofuran or N,N-dimethylformamide. The hydrogenolysis of the benzyl ester is preferably carried out in an aqueous-alcoholic solvent, more especially in ethanol.

The examples which follow are illustrations of the compounds of the general formula I and the various methods of preparation detailed above, but in no way restrict the scope of the present invention. All the products obtained were analyzed by thin layer chromatography, showing only a single spot. The thin layer chromatography (TLC) was performed on an F 254 silica gel plate and developed in the following systems in the case of the products of the general formula I:

A: toluene 10; formic acid 1; ethyl formate 10
B: CHCl$_3$ 95; acetone 5 and revealed under ultraviolet light at 254 nm. The results of the percentage analyses carried out on all the products are consistent with the theoretical formulae.

Apart from a very marked antiviral activity, all the products obtained also possess hypocholesterolemic, hypobetalipoproteinemic and anticonvulsant properties.

PREPARATION EXAMPLES
EXAMPLE I

N-[Adamantan-1-yl]-(L)-Pyroglutamide (I; R=H)

(1) Via an N-protected pyroglutamic acid chloride (a) N-benzyloxycarbonyl-(L)-glutamic acid 400 g (2.72 mol) of (L)-glutamic acid are dissolved in 2.66 liters of 2N sodium hydroxide solution, the resulting solution is cooled to 5° C. and about 400 ml of benzyl chloroformate (3.6 mol) are run in slowly, dilute sodium hydroxide solution (1 to 2N) being added simultaneously to keep the pH at around 9.0. The mixture is stirred for a few hours, washed with 2×200 ml of ether and acidified to around pH 1. After extraction with ethyl acetate, washing several times with a saturated aqueous solution of sodium chloride, drying and evaporation, a thick oil is obtained which crystallizes from hexane. Weight=500 g; yield=65%; melting point=116/7° C.; H+titer=99%; $[\alpha]_D^{22} = -10.4°$ (1%, acetone).

(b) N-nenzyloxycarbonyl-(L)-glutamic anhydride 500 g of N-(Cbo)-glutamic acid (1.78 mol) are dissolved in 3.5 liters of THF at room temperature and 361 g of dicyclohexylcarbodiimide dissolved in 1.75 liters of THF are added, with stirring. Dicyclohexylurea precipitates rapidly, the mixture is stirred overnight and the urea is then filtered off. The filtrate is evaporated to dryness and the residual thick oil is taken up in 6 to 8 times its own weight of a 90/10 mixture of ether and chloroform. After a few days in a refrigerator, the crystals formed are filtered off. Dry weight ≧400 g; yield=85% to 90%; melting point=90/91° C.; $[\alpha]_D^{22} = -41.5°$ (2%, acetic acid).

(c) dicyclohexylamine salt of N-benzyloxycarbonyl-(L)-pyroglutamic acid 400 g (1.52 mol) of N-benzyloxycarbonyl-(L)-glutamic anhydride are suspended in 1.5 liters of THF and 4 liters of ether at ordinary temperature and a solution of 300 ml of dicyclohexylamine (1.52 mol) in 500 ml of ether is run in very slowly.

The dicyclohexylamine (DCHA) salt precipitates as the solution is run in. After stirring overnight, it is filtered off and dried.

The yield of a white product of melting point 206/208° C. is quantitative. The 735 g of crude product are recrystallized from 7 to 8 volumes of ethanol.

(d) N-benzyloxycarbonyl-(L)-pyroglutamic acid chloride 50 g (0.113 mol) of the previously obtained dicyclohexylamine salt of N-benzyloxycarbonyl-(L)-pyroglutamic acid are mixed to a paste with 1 liter of toluene, 110 ml of thionyl chloride are run in dropwise and the temperature is then raised to 60° C. for 2 hours. The mixture is cooled and filtered, the filtrate is evaporated and the residue is taken up several times with benzene. The acid chloride finally crystallizes from petroleum ether with a practically quantitative yield. Melting point=65°-70° C. (literature=71/72° C.).

(e) N₁-benzyloxycarbonyl-N-(adamantan-1-yl)-(L)-pyroglutamide 25 g (0.165 mol) of adamantanamine and 17 ml of triethylamine are dissolved in 450 ml of chloroform at ordinary temperature and a solution of 45 g (0.16 mol) of previously prepared N-(Cbo)-pyroglutamic acid chloride in 450 ml of chloroform is run in slowly over 3 hours. Completion of the reaction is monitored by TLC and the organic layer is washed with water, dilute sodium hydroxide solution, dilute hydrochloric acid and then water again. After drying, the chloroform is evaporated off and the crude product is recrystallized from 600 ml of ethanol. This gives 55% of a product of melting point 186/7° C. and 13% of a product of melting point 182/3° C.

(f) N-(adamantan-1-yl)-(L)-pyroglutamide 35 g of N₁-benzyloxycarbonyl-N-(adamantan-1-yl)-pyroglutamide are hydrogenated in 350 ml of ethanol at ordinary temperature and pressure, in the presence of 2 g of palladium/charcoal. When the hydrogenation has ended, the mixture is filtered, the filtrate is evaporated and the residue is recrystallized from an ethyl acetate-/acetone mixture to give 78% of a pure product of melting point 194/5° C. and $[\alpha]_D^{22} = -56°$ (C=1, chloroform), having the following characteristics:

IR: NH 3310 cm⁻¹ (vs); CONH 1640 cm⁻¹ and 1530 cm⁻¹ (vs).

NMR: NH (s) (2H) at 7.6 and 6.1 ppm; CH—CO (m) (1H) at 4.2 ppm; CH₂—CH₂ (pyrrolidone) (m) (4H) at 2.4 ppm; adamantane (2m) (15H) at 2.2 and 1.8 ppm.

(2) Via the N-substituted reactive esters of (L)-pyroglutamic acid (a) paranitrophenyl N-(benzyloxycarbonyl)-(L)-pyroglutamate 10 g (40 mmol) of N-(benzyloxycarbonyl)-(L)-pyroglutamic acid and 5.84 g (40 mmol) of p-nitrophenol are dissolved in 100 ml of THF. A solution of 8.65 g (42 mmol) of N,N-dicyclohexylcarbodiimide in 40 ml of THF is run in at ordinary temperature, the mixture is stirred for 6 hours and filtered, the filtrate is evaporated, the residue is taken up with ethyl acetate, the mixture is filtered, the filtrate is evaporated and the residue is recrystallized from the same solvent. This gives 60% of a pure product of melting point=141°-2° C.; $[\alpha]_D^{25} = -48.7°$ (C=1, THF).

(b) N₁-benzyloxycarbonyl-N-(adamantan-1-yl)-(L)-pyroglutamide 20 mmol of the above reactive ester and 21 mmol of adamantanamine are stirred for 8 hours in a mixture of 20 ml of N,N-dimethylformamide and 80 ml of tetrahydrofuran. The resulting mixture is filtered, the filtrate is evaporated to dryness and the residue is recrystallized from ethanol as described in detail in Example (1)(e). The preparation is completed according to (1)(f) to give the desired product with a yield of about 60%.

The same procedure can be followed to give the corresponding pentachlorophenyl ester, which can be used to give the amide described under (2)(b) and then the amide described under (1)(f) with a yield of about 55%.

(3) Via a mixed anhydride of unprotected (L)-pyroglutamic acid (R=H)

(a) Use of pivaloyl chloride: $(CH_3)_3C-COCl$ 10 g of (L)-pyroglutamic acid (77 mmol) and 10.7 ml of triethylamine are mixed with 100 ml of anhydrous acetone, 9.29 g of pivaloyl chloride (77 mmol) are run in slowly at −5° and then, after 15 minutes at 0° C., 11.65 g (77 mmol) of adamantanamine are added in several portions.

The very thick medium slowly becomes fluid and, after 5 hours at 0° C., the solvent is evaporated off, the residue is taken up with chloroform and the mixture is washed copiously with water. After drying and evaporation, the residue is recrystallized from acetone. This gives a product with a yield of 30%, the physical and spectroscopic characteristics of which correspond to those noted in Example (1)(f).

EXAMPLE II $N_1$-Acetyl-N-(adamantan-1-yl)-(L)-pyroglutamide

(1) benzyl (L)-pyroglutamate

A suspension of 103.2 g (0.8 mol) of (L)-pyroglutamic acid in 2.8 liters of toluene, 86.6 g (0.8 mol) of benzyl alcohol and 4.3 ml of sulfuric acid is heated under reflux for 7 to 8 hours in a 4 liter apparatus equipped with a good stirrer and a Dean-Stark attachment. TLC (A) is used to check that the benzyl alcohol has disappeared and the mixture is cooled and washed with 2×400 ml of water, 2×400 ml of a 2% solution of $Na_2CO_3$ and then 2×400 ml water. The toluene layer is dried over sodium sulfate and evaporated in vacuo and the residue is dried in vacuo in the presence of $P_2O_5$. This gives 70 to 75% of a pure product of Rf=0.5 (A) and melting point=48°–49° C. The product can also be distilled; boiling point=170°–5° C. (0.1 mm Hg).

(2) benzyl N-acetyl-(L)-pyroglutamate

A solution of 61.3 g (280 mmol) of benzyl (L)-pyroglutamate in 400 ml of benzene is added over 2 hours to a suspension of 13.4 g of NaH (280 mmol) in 50 ml of dry benzene. After stirring for one hour at ordinary temperature, a solution of 22.7 g (290 mmol) of acetyl chloride in 150 ml of benzene is run in and the mixture is heated at 55° for 5 hours and then stirred for 24 hours at ordinary temperature, washed with 2×150 ml of water, dried and evaporated. The product is distilled under reduced pressure; boiling point=150°–60° C. (0.25 mm Hg). This gives 60% of a pure product of Rf=0.63 (A).

(3) N-acetyl-(L)-pyroglutamic acid 43.6 g (167 mmol) of the previously obtained product are hydrogenated at atmospheric pressure in 400 ml of ethanol, in the presence of 2 g of 5% palladium/C. After the catalyst has been filtered off, the filtrate is evaporated to dryness, the residue is taken up with benzene, the mixture is evaporated to dryness and the residue is dried under high vacuum for 24 hours. This gives a quantitative yield of a pure oily product of Rf=0.33 (A), revealed with UV 254 nm and iodine.

This product can be converted to the dicyclohexylamine salt, which can be recrystallized from an ethanol/ethyl acetate mixture; melting point=172°–3° C.

(4) $N_1$-acetyl-N-(adamantan-1-yl)-(L)-pyroglutamide

A solution of 15.4 g (90 mmol) of the previously obtained acid in 40 ml of pure chloroform is run into 120 g (1 mol) of thionyl chloride. The mixture is stirred at 50° C. for 2 hours and then evaporated, the residue is taken up several times with chloroform, the mixture is evaporated, the residue is taken up in 80 ml of chloroform and the mixture is run into a suspension of 27.2 g (180 mmol) of adamantanamine in 250 ml of chloroform and 7.1 g (90 mmol) of pyridine.

The mixture is heated under reflux for 4 hours and then stirred at ordinary temperature for 15 hours, cooled to about 0° C. and filtered, the filtrate is evaporated to dryness, the residue is taken up with iced 0.5N hydrochloric acid (200 ml), extraction is carried out with benzene and the extract is washed with 150 ml of 0.5N hydrochloric acid, 2×150 ml of water, 2×125 ml of 1% sodium bicarbonate and 3×150 ml of water. After the benzene layer has been dried and evaporated, the residue is recrystallized from isopropyl alcohol (4 volumes). This gives 35% of a pure product of Rf=0.38 (A).

NMR spectrum in $CDCl_3$ solution relative to TMS: at 5.9 ppm (s), broad, 1H, NH; 4.5 ppm (m), 1H, CH—CONH; 2.4 to 2.8 ppm (m), 4H, $CH_2-CH_2$ (pyrrolidone); 2.5 ppm (s), 3H, $CH_3CO$; 1.7 and 2.1 ppm (2s), 15H (adamantane).

EXAMPLE III $N_1$-Cyclopentylpropionyl-N-(adamantan-1-yl)-(L)-pyroglutamide

(1) benzyl $N_1$-cyclopentylpropionyl-(L)-pyroglutamate

A solution of 18.6 g (85 mmol) of benzyl (L)-pyroglutamate, prepared according to Example II-(1), in 150 ml benzene is added over 1 hour to a suspension of 4.1 g of sodium hydride (85 mmol) in 15 ml of dry benzene. After stirring for 1 hour at ordinary temperature, a solution of 13.7 g (85 mmol) of cyclopentylpropionyl chloride in 150 ml of benzene is run in and the mixture is heated at 50° C. for 5 hours and then stirred for 18 hours at ordinary temperature, washed with 2×100 ml of water, dried and evaporated. The product is purified by chromatography on a silica column using a chloroform/acetone mixture as the eluent. This gives 73% of a pure oily product showing only a single spot in TLC: Rf=0.80 (A).

(2) N-cyclopentylpropionyl-(L)-pyroglutamic acid 21.3 g (62 mmol) of the previously obtained product are hydrogenated at atmospheric pressure in 220 ml of ethanol, in the presence of 1 g of 5% palladium/C. After the catalyst has been filtered off, the filtrate is evaporated to dryness and the residue is taken up several times with benzene and dried under high vacuum (0.05 mm Hg) for 24 hours. This gives a 93% yield of a pure product of Rf=0.05 (A) and melting point=135°–8° C.

(3) $N_1$-cyclopentylpropionyl-N-(adamantan-1-yl)-(L)-pyroglutamide

A solution of 11.38 g (45 mmol) of the previously obtained acid in 30 ml of chloroform is run into 65 g (0.55 mol) of thionyl chloride. The mixture is stirred at 50° C. for 2 hours and evaporated to dryness, the residue is taken up several times with chloroform, the mixture is evaporated, the residue is taken up in 50 ml of chloroform and the mixture is run into a suspension of 13.6 g (90 mmol) of adamantanamine in 120 ml of chloroform and 3.55 g (45 mmol) of pyridine. The mixture is heated under reflux for 4 hours and then stirred at ordinary temperature for 15 hours, cooled to about 0° and filtered, the filtrate is evaporated and the residue is taken up with 120 ml of iced 0.5N hydrochloric acid. Extraction is carried out with benzene and the extract is washed in the usual manner (as in Example II(4), dried and evaporated. The residue is recrystallized from isopropanol (6 volumes). This gives 40% of a pure product of Rf=0.53 (A) and melting point=169°-70° C.

NMR spectrum in CDCl$_3$ solution relative to TMS: at 6.1 ppm (s), broad, 1H, NH; at 4.5 ppm (m), 1H, C$\underline{H}$—CONH; 2.4 to 2.8 ppm (m), 4H, C$\underline{H_2}$—C$\underline{H_2}$, pyrrolidone; 2.2 ppm (m), 2H,

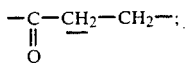

1.7 and 2.1 ppm (2s), 15H, adamantane; 1.1 to 1.6 ppm (m), 11H, unresolved cyclopentyl signals.

EXAMPLE IV

N$_1$-Dipropylacetyl-N-[adamantan-1-yl]-(L)-pyroglutamide (1) benzyl N-dipropylacetyl-(L)-pyroglutamate 50.3 g (230 mmol) of benzyl (L)-pyroglutamate, prepared according to Example II(1), are dissolved in 200 ml of chloroform and 36.3 g (359 mmol) of triethylamine at ordinary temperature. A solution of 37.4 g (230 mmol) of dipropylacetyl chloride in 50 ml of chloroform is run in and the mixture is heated under reflux for 5 hours.

After cooling, the mixture is washed with water, dried and evaporated, the residue is taken up in hexane and the product is purified by chromatography on an alumina column using hexane as the eluent. This gives a pure oily product of Rf=0.7 (A).

(2) N-dipropylacetyl-(L)-pyroglutamic acid 79.4 g (230 mmol) of the previously obtained ester are hydrogenated at atmospheric pressure in 800 ml of isopropyl alcohol, in the presence of 8 g of 5% palladium/C. After the catalyst has been filtered off, the filtrate is evaporated to dryness, the residue is taken up several times with benzene and the mixture is evaporated to dryness. This gives 95% of a pure oily product of Rf=0.50 (A). It can be converted to the piperazine salt (1/1), which is crystallized from an ethyl ether/acetone mixture; melting point=128°-30° C.; $[\alpha]_D^{22}=-37.2°$ (C=1, water).

(3) N$_1$-dipropylacetyl-N-(adamantan-1-yl)-(L)-pyroglutamaide

A solution of 11.48 g (45 mmol) of the previously obtained acid in 30 ml of chloroform is run into 65 g (0.55 mol) of thionyl chloride. The mixture is stirred at 50° C. for 2 hours and evaporated to dryness, the residue is taken up several times with benzene, the mixture is evaporated, the residue is taken up in 50 ml of chloroform and the mixture is run into a suspension of 13.6 g (90 mmol) of adamantanamine in 120 ml of chloroform and 3.55 g (45 mmol) of pyridine. The mixture is heated under reflux for 5 hours and then stirred at room temperature for 15 hours, cooled and filtered and the filtrate is evaporated. The residue is taken up with 120 ml of iced 0.5N hydrochloric acid, extraction is carried out with benzene and the extract is washed in the usual manner (cf. Example II-4), dried and evaporated. The residue is recrystallized from isopropanol. This gives 45% of a pure product; Rf=0.55 (A); Rf=0.55 (B); melting point=155°-7° C.

NMR spectrum in CDCl$_3$ solution relative to TMS: at 6.0 ppm (s), broad, 1H, NH; at 4.6 ppm (m), 1H, C$\underline{H}$—CONH; at 3.7 ppm (m), 1H, C$\underline{H}$—CO—; at 2.2-2.7 ppm (m), 4H, C$\underline{H_2}$—C$\underline{H_2}$, pyrrolidone; at 1.7 and 2.1 ppm (2s), 15H, adamantane; 0.8 to 1.8 ppm (m), 14H, C$\underline{H_2}$, C$\underline{H_3}$.

EXAMPLE V

N$_1$-[2-Ethylhexanoyl]-N-[adamantan-1-yl]-(L)-pyroglutamide (1) benzyl N-[2-ethylhexanoyl]-(L)-pyroglutamate 39.4 g (180 mmol) of benzyl (L)-pyroglutamate, prepared according to Example II(1), are dissolved in 160 ml of chloroform and 28.4 g (28 mmol) of triethylamine at ordinary temperature. A solution of 29.3 g (180 mmol) of 2-ethylhexanoyl chloride in 40 ml of chloroform is run in and the mixture is heated under reflux for 5 hours.

After cooling, the mixture is washed with water, dried and evaporated and the residue is purified by chromatography on a silica column using benzene as the eluent. This gives 80% of a pure oily product of Rf=0.70 (A).

(2) N-[2-ethylhexanoyl]-(L)-pyroglutamic acid 48.3 g (140 mmol) of the previously obtained ester are hydrogenated at atmospheric pressure in 500 ml of isopropyl alcohol, in the presence of 5 g of 5% palladium/C. After the catalyst has been filtered off, the filtrate is evaporated to dryness, the residue is taken up several times with benzene and the mixture is evaporated to dryness. This gives 95% of a pure oily product of Rf=0.50 (A). The product can be converted to the piperazine salt (1/1) by dissolution of equimolecular quantities in ether (650 ml/100 mmol) under reflux and crystallization in the cold: melting point=110°-2° C.; $[\alpha]_D^{22}=-44.5°$ (C=1; water).

(3) N$_1$-(2-ethylhexanoyl)-N-(adamantan-1-yl)-(L)-pyroglutamide

A solution of 16.06 g (63 mmol) of the previously obtained acid in 40 ml of chloroform is run into 91 g (765 mmol) of thionyl chloride. The mixture is stirred at 50° C. for 2 hours and evaporated to dryness, the residue is taken up several times with benzene, the mixture is evaporated, the residue is taken up in 70 ml of chloroform and the mixture is run into a suspension of 19.1 g (126 mmol) of adamantanamine in 170 ml of chloroform and 4.98 g (63 mmol) of pyridine. The mixture is heated under reflux for 5 hours and then stirred at room temperature for 15 hours, cooled and filtered and the filtrate is evaporated. The residue is taken up in 170 ml of iced 0.5N hydrochloric acid, extraction is carried out with benzene and the extract is washed in the usual manner (cf. Example II(4) and dried. After evaporation, the product obtained is recrystallized from isopropanol.

This gives 40% of a pure product of Rf=0.55 (A), Rf=0.55 (B) and melting point=150°-2° C.

NMR spectrum in CDCl$_3$ solution relative to TMS: identical to that detailed for the previous product, Example IV(3).

EXAMPLE VI

N$_1$-Hexanoyl-N-(adamantan-1-yl)-(L)-pyroglutamide (1) benzyl N-hexanoyl-(L)-pyroglutamate A solution of 17.5 g (80 mmol) of benzyl (L)-pyroglutamate, prepared according to Example II(1), in 150 ml of benzene is added over 1 hour to a suspension of 3.85 g (80 mmol) of sodium hydride in 15 ml of dry benzene. After stirring for 1 hour at ordinary temperature, a solution of 10.9 g (81 mmol) of hexanoyl chloride in 140 ml of benzene is run in. The mixture is heated at 50° C. for 5 hours and then stirred at ordinary temperature for 15 hours, washed with water (2×100 ml), dried and evaporated.

The residue is purified by chromatography on a silica column using chloroform as the eluent. This gives 62% of a pure oily product of Rf=0.71 (A) and Rf=0.90 (B).

(2) N-hexanoyl-(L)-pyroglutamic acid 14.3 g (45 mmol) of the previously obtained product are hydrogenated in 150 ml of ethanol, in the presence of 1 g of 5% palladium/C. After the catalyst has been filtered off, the filtrate evaporated and the residue taken up several times with benzene, the product is dried under high vacuum (0.05 mm Hg) for 24 hours. This gives a 92% yield of a pure product of Rf=0.48 (A) and melting point=85°-90° C.

(3)
N$_1$-hexanoyl-N-(adamantan-1-yl)-(L)-pyroglutamide

A solution of 9.08 g (40 mmol) of the previously obtained acid in 30 ml of chloroform is run into 58.3 g (0.49 mol) of thionyl chloride. The mixture is stirred at 50° C. for 2 hours and evaporated to dryness, the residue is taken up several times with benzene, the mixture is evaporated, the residue is taken up in 50 ml of chloroform and the mixture is run into a suspension of 12.10 g (80 mmol) of adamantanamine in 110 ml of chloroform and 3.17 g (40 mmol) of pyridine. The mixture is heated under reflux for 5 hours and then stirred at ordinary temperature for 15 hours, cooled to about 0° C. and filtered and the filtrate is evaporated. The residue is taken up in 110 ml of iced 0.5N hydrochloric acid, extraction is carried out with benzene and the extract is washed in the usual manner (cf. Example II(4) and dried. After evaporation, the residue is recrystallized from isopropyl alcohol. This gives 65% of a pure product of Rf=0.52 (A) and melting point=132°-4° C.

NMR spectrum in CDCl$_3$ solution relative to TMS: at 6.0 ppm (s), broad, 1H, NH; at 4.6 ppm (m), 1H, CHCONH; 2.4 to 2.8 ppm (m), 6H, CH$_2$—CH$_2$ (pyrrolidone) and —CH$_2$CON; 1.7 to 2.1 ppm (m), 15H, adamantane; 1.3 to 1.7 ppm (m), 6H, —CH$_2$—CH$_2$—CH$_2$—CH$_3$; 0.85 ppm (t), 3H, CH$_3$—CH$_2$—.

EXAMPLE VII

N$_1$-Benzoyl-N-(adamantan-1-yl)-(L)-pyroglutamide (1) benzyl N-benzoyl-(L)-pyroglutamate A solution of 21.9 g (0.1 mol) of benzyl (L)-pyroglutamate (prepared according to Example II(1)) in 150 ml of benzene is added over an hour to a suspension of 4.8 g (0.1 mol) of sodium hydride in 15 ml of dry benzene. The mixture is stirred for one hour at ordinary temperature and 14.1 g (0.1 mol) of benzoyl chloride diluted in benzene are then introduced. The reaction mixture is stirred for 4 hours at 55° C. and then for 18 hours at ordinary temperature. After the mixture has been washed with water, the solvent evaporated off and the residue taken up with ether, white crystals of melting point=101°/2° C. are obtained; yield=70%; Rf=0.68 (A).

(2) N-benzoyl-(L)-pyroglutamic acid 19.4 g (60 mmol) of the previously obtained ester are hydrogenated at atmospheric pressure in 350 ml of ethanol at 40° C., in the presence of 2 g of 5% palladium/C. After the catalyst has been filtered off, the filtrate is evaporated to dryness. The residue is recrystallized from 7 to 8 volumes of ethanol. This gives 87% of a pure product; Rf=0.53 (A); melting point=140°-1° C.

(3) N$_1$-benzoyl-N-(adamantan-1-yl)-(L)-pyroglutamide 11.65 g (50 mmol) of the previously obtained acid are dispersed in 77 g (0.65 mol) of thionyl chloride, the dispersed acid is solubilized at 40° C., the solution is stirred for 1 hour and evaporated and the residue is taken up with dry ether. After filtration, a cream-colored powder is obtained with a yield of 81%. A solution of 10.1 g (40 mmol) of the previously obtained acid chloride in 180 ml of chloroform is added to a suspension of 12.1 g (80 mmol) of adamantanamine in 130 ml of chloroform and 3.17 g (40 mmol) of pyridine. The mixture is heated under reflux for 3 hours and stirred at ordinary temperature for 15 hours, cooled and filtered and then, after washing several times in the usual manner (cf. Example II(4)), the filtrate is dried and evaporated. The residue is triturated in ether, filtered off and then recrystallized from isopropyl alcohol (13 volumes). This gives 52% of a pure product; Rf=0.60 (A); Rf=0.32 (B); melting point=196°-7° C.; [α]$_D$=−4.4° (C=1, CHCl$_3$).

NMR spectrum in CDCl$_3$ solution relative to TMS: 7.25 to 7.70 ppm (m), 5H, C$_6$H$_5$CO; 5.85 ppm (s), broad, 1H, NH; 4.60 ppm (m), 1H, CHCONH; 2.40 to 2.85 ppm (m), 4H, CH$_2$—CH$_2$, pyrrolidone; 1.7 and 2.05 ppm (2s), 15H, adamantane.

EXAMPLE VIII

N$_1$-Paramethoxybenzoyl-N-(adamantan-1-yl)-(L)-pyroglutamide (1) benzyl N-paramethoxybenzoyl-(L)-pyroglutamate A solution of 18.6 g (85 mmol) of benzyl (L)-pyroglutamate, prepared according to Example II(1), in 150 ml of benzene is added over 1 hour to a suspension of 4.08 g (85 mmol) of sodium hydride in 15 ml of dry benzene. After stirring for 1 hour at ordinary temperature, a solution of 14.7 g (86 mmol) of p-mthoxybenzoyl chloride in 150 ml of benzene is run in. The mixture is heated at 50° C. for 5 hours, stirred at ordinary temperature for 18 hours, washed with water (2×100 ml), dried and evaporated. The residue is purified by chromatography on a silica column using a mixture of methylene chloride and ether (0.5%) as the eluent.

This gives 50% of a pure oily product of Rf=0.68 (A) and Rf=0.90 (B).

(2) N-p-methoxybenzoyl-(L)-pyroglutamic acid 14.1 g (40 mmol) of the previously obtained product are hydrogenated in 200 ml of ethanol at 40°, in the presence of 1.2 g of 5% palladium/C. After the catalyst has been filtered off and the filtrate evaporated, the residue is triturated with ether and the ether is evaporated off. This gives 93% of a pure product of Rf=0.52 (A), melting point=149°-50° C. and $[\alpha]_D=+59.5°$ (C=1, DMF).

(3) $N_1$-p-methoxybenzoyl-N-(adamantan-1-yl)-(L)-pyroglutamide

A solution of 9.2 g (35 mmol) of the previously obtained acid in 10 ml of chloroform is run into 51.2 g (0.43 mol) of thionyl chloride; the mixture is stirred at 50° C. for 2 hours and evaporated to dryness, the residue is taken up several times with benzene, the mixture is evaporated, the residue is taken up in 50 ml of chloroform and the mixture is run into a suspension of 10.6 g (70 mmol) of adamantanamine in 100 ml of chloroform and 2.77 g (35 mmol) of pyridine. The mixture is kept under reflux for 4 hours and then at ordinary temperature for 15 hours, cooled and filtered and the filtrate is evaporated. The residue is taken up with 140 ml of iced 0.5N hydrochloric acid and extraction is carried out with benzene. After the benzene layer has been washed several times in the conventional manner (Example II(4)), it is dried and the evaporation residue is recrystallized from the minimum quantity of isopropyl alcohol to give 41% of a pure product. Rf=0.42 (A); melting point=197°-9° C.

NMR spectrum in CDCl$_3$ solution relative to TMS: 7.65 ppm (d), 2H, aromatic H ortho to —CON; 6.90 ppm (d), 2H, aromatic H ortho to OCH$_3$; 5.70 ppm (s), broad, 1H, NH; 4.55 ppm (m), 1H, CHCONH; 3.80 ppm (s), 3H, OCH$_3$; 2.40 to 2.85 ppm, 4H, CH$_2$CH$_2$, pyrrolidone; 1.65 and 2.05 ppm (2s), 15H, adamantane.

EXAMPLE XI $N_1$-[3,4-dimethoxybenzoyl]-N-[adamantan-1-yl]-(L)-pyroglutamide

(1) benzyl N-(3,4-dimethoxybenzoyl)-(L)-pyroglutamate

A solution of 24.1 g (0.11 mol) of benzyl (L)-pyroglutamate, prepared according to Example II(1), in 200 ml of benzene is added over 1½ hours to a suspension of 5.28 g (0.11 mol) of sodium hydride in 20 ml of dry benzene. After stirring for 1 hour at ordinary temperature, a solution of 22.1 g (0.11 mol) of 3,4-dimethoxybenzoyl chloride in 180 ml of benzene is run in.

The mixture is heated at 55° C. for 5 hours and then stirred at ordinary temperature for 18 hours, washed with water (2×150 ml), dried and evaporated. The residue is purified by chromatography on a silica column using a methylene chloride/ether mixture as the eluent. This gives 40% of a pure product of Rf=0.65 (A) and Rf=0.60 (B).

(2) N-(3,4-dimethoxybenzoyl)-(L)-pyroglutamic acid 15.3 g (40 mmol) of the previously obtained ester are hydrogenated at atmospheric pressure in 250 ml of ethanol at 45° C., in the presence of 1.5 g of 5% palladium/C. After the catalyst has been filtered off, the filtrate evaporated, the residue taken up with benzene and the mixture evaporated, the product is triturated with ether and then filtered off. This gives 75% of a pure product of melting point=152°-3° C. and Rf=0.28 (A).

(3) $N_1$-(3,4-dimethoxybenzoyl)-N-(adamantan-1-yl)-(L)-pyroglutamide 8.8 g (30 mmol) of the previously obtained acid are added in portions to 44 g (0.37 mol) of thionyl chloride. The mixture is stirred for 2 hours at 50° C. and evaporated to dryness, the residue is taken up several times with benzene, the mixture is evaporated, the residue is taken up in 70 ml of chloroform and the mixture is run into a suspension of 9.08 g (60 mmol) of adamantanamine in 80 ml of chloroform and 2.4 g (30 mmol) of pyridine. The mixture is heated under reflux for 4 hours and stirred at ordinary temperature for 15 hours, cooled and filtered and the filtrate is evaporated. The residue is taken up in 0.5N hydrochloric acid and extraction is carried out and the extract washed in the usual manner (cf. Example II(4)). After evaporation of the benzene layer, the product is purified by chromatography on a silica column using a chloroform/acetone mixture as the eluent, followed by recrystallization from an isopropyl alcohol/ether mixture. This gives 35% of a pure product; Rf=0.33 (A); Rf=0.18 (B); melting point=205°-7° C.

NMR spectrum in CDCl$_3$ solution relative to TMS: 6.90 to 7.40 ppm (m), 3H, aromatic H; 5.75 ppm (s), broad, 1H, NH; 4.50 ppm (m), 1H, CHCONH; 3.80 and 3.85 ppm (2s), 6H, OCH$_3$; 2.20 and 2.70 ppm (m), 4H, CH$_2$—CH$_2$, pyrrolidone; 1.65 and 2.05 ppm (2s), 15H, adamantane.

EXAMPLE X $N_1$-[phenylacetyl]-N-[adamantan-1-yl]-(L)-pyroglutamide

(1) benzyl $N_1$-[phenylacetyl]-(L)-pyroglutamate

A solution of 18.6 g (85 mmol) of benzyl (L)-pyroglutamate, prepared according to Example II(1), in 150 ml of benzene is added over 1 hour to a suspension of 4.1 g (85 mmol) of sodium hydride in 15 ml of dry benzene.

After stirring for 1 hour at ordinary temperature, a solution of 13.3 g (86 mmol) of phenylacetyl chloride in 150 ml of benzene is run in. The mixture is heated for 5 hours at 55° C. and then stirred for 15 hours at ordinary temperature, washed with water (2×120 ml), dried and evaporated. The residue is purified by chromatography on a silica column using chloroform as the eluent. This gives 58% of a pure oily prudct of Rf=0.72 (A) and Rf=0.90 (B).

(2) N-phenylacetyl-(L)-pyroglutamic acid 15.2 g (45 mmol) of the previously obtained ester are hydrogenated at atmospheric pressure in 200 ml of ethanol at ordinary temperature, in the presence of 1.5 g of 5% palladium/C. After the catalyst has been filtered off, the filtrate is evaporated to dryness, the residue is taken up several times with benzene, the mixture is evaporated and the residue is dried under high vacuum (0.05 mm Hg). This gives 95% of a pure waxy product of Rf=0.42 (A).

(3)

N₁-(phenylacetyl)-N-(adamantan-1-yl)-(L)-pyroglutamide

A solution of 9.9 g (40 mmol) of the previously obtained acid in 40 ml of chloroform is run into 59 g (0.49 mol) of thionyl chloride. The mixture is stirred at 50° C. for 2 hours and evaporated to dryness, the residue is taken up several times with benzene, the mixture is evaporated, the residue is taken up in 60 ml of chloroform and the mixture is run into a suspension of 12.1 g (80 mmol) of adamantanamine in 100 ml of chloroform and 3.17 g (40 mmol) of pyridine. The mixture is heated under reflux for 5 hours and then stirred at ordinary temperature for 15 hours, cooled and filtered and the filtrate is evaporated. The residue is taken up in 0.5N hydrochloric acid and extraction is carried out and the extract washed in the usual manner (cf. Example II(4)). After drying and evaporation, the residue is purified by chromatography on a silica column using a chloroform/acetone mixture as the eluent. This gives 45% of a pure product of Rf=0.50 (A), Rf=0.45 (B) and melting point=130°-2° C.

NMR spectrum in CDCl₃ solution relative to TMS: 7.25 ppm (s), 5H, C₆H₅; 5.80 ppm (s), broad, 1H, NH; 4.50 ppm (m), 1H, CHCONH; 2.40 to 2.90 ppm (m), 4H, —CH₂—CH₂—, pyrrolidone; 1.70 and 2.0 ppm (2s), 15H, adamantane.

EXAMPLE XI

N₁-(3,4-dimethoxyphenylacetyl)-N-adamantan-1-yl)-(L)-pyroglutamide (1) benzyl N-(3,4-dimethoxyphenylacetyl)-(L)-pyroglutamate A solution of 17.5 g (80 mmol) of benzyl (L)-pyroglutamate, prepared according to Example II(1), in 150 ml of benzene is added over 1 hour to a suspension of 3.85 g (80 mmol) of sodium hydride in 15 ml of dry benzene. After stirring for 1 hour at ordinary temperature, a solution of 17.2 g (80 mmol) of 3,4-dimethoxyphenylacetyl chloride in 150 ml of benzene is run in. The mixture is heated at 55° C. for 6 hours and stirred at ordinary temperature for 15 hours, washed with 2×120 ml of water, dried and evaporated. The residue was purified by chromatography on a silica column using a chloroform/acetone mixture as the eluent. Thus gives 60% of a pure waxy product of Rf=0.46 (A).

(2) N-3,4-dimethoxyphenylacetyl-(L)-pyroglutamic acid 19.9 g (50 mmol) of the previously obtained acid are hydrogenated at ordinary temperature and atmospheric pressure in 300 ml of ethanol, in the presence of 2 g of 5% palladium/C.

After the catalyst has been filtered off, the filtrate is evaporated, the residue is taken up several times with benzene, the mixture is evaporated to dryness and the residue is dried under high vacuum (0.05 mm Hg). This gives 93% of a pure waxy product of Rf=0.33 (A).

(3)

N₁-(3,4-dimethoxyphenylacetyl)-N-(adamantan-1-yl)-(L)-pyroglutamide

A solution of 13.8 g (44 mmol) of the previously obtained acid in 35 ml of chloroform is run into 65.5 g (550 mmol) of thionyl chloride; the mixture is kept at 50° C. for 2 hours and evaporated to dryness, the residue is taken up several times with benzene, the mixture is evaporated to dryness, the residue is taken up with 50 ml of chloroform and the mixture is run into a suspension of 13.6 g (90 mmol) of adamantanamine in 120 ml of chloroform and 3.6 g (45 mmol) of pyridine. The mixture is heated under reflux for 6 hours and stirred at ordinary temperature for 15 hours, cooled and filtered and the filtrate is evaporated. The residue is treated in the usual manner (cf. Example II(4)). After evaporation of the benzene layer, the product is purified by chromatography on a silica column using a chloroform/acetone mixture as the eluent. This gives 35% of a pure product; Rf=0.42 (A); Rf=0.31 (B); melting point=7-5°-7° C.

NMR spectrum in CDCl₃ solution relative to TMS: 6.80 ppm (s), 3H, (OCH₃)₂C₆H₃—CH₂; 5.75 ppm (s), broad, 1H, NH; 4.55 ppm (m), 1H, CHCONH; 4.2 ppm (s), 2H, CH₂CON; 3.85 ppm (s), 6H, OCH₃×2; 2.40 to 2.85 ppm (m), 4H, —CH₂CH₂—, pyrrolidone; 1.60 and 1.95 ppm (2s), 15H, adamantane.

EXAMPLE XII

N₁-[2-methoxyethyl]-N-[adamantan-1-yl]-(L)-pyroglutamide (1) benzyl N-(2-methoxyethyl)-(L)-pyroglutamate A solution of 28.5 g (0.13 mol) of benzyl (L)-pyroglutamate, prepared according to Example II(1), in 200 ml of N,N-dimethylformamide is added over 1.5 hours to a suspension of 6.24 g (0.13 mol) of solution hydride in 30 ml of N,N-dimethylformamide. The mixture is stirred for 1 hour at ordinary temperature and a solution of 14.7 g (156 mmol) of 2-methoxyethyl chloride in 100 ml of dimethylformamide is then run in. The mixture is heated at 70° C. for 5 hours and stirred at ordinary temperature for 15 hours and evaporated to dryness, the residue is taken up with 200 ml of 0.5N hydrochloric acid, extraction is carried out with benzene and the extract is washed with water and dried. After evaporation of the benzene layer, the residue is purified by chromatography on a silica column using a methylene chloride/ether mixture as the eluent. This gives 45% of a pure product of Rf=0.45 (A).

(2) N-(2-methoxyethyl)-(L)-pyroglutamic acid 15.2 g (55 mmol) of the previously obtained ester are hydrogenated at ordinary temperature and atmospheric pressure in 200 ml of ethanol, in the presence of 1.5 g of 5% palladium/C. After the catalyst has been filtered off, the filtrate evaporated and the residue taken up several times with benzene, the resulting residue is dried under high vacuum (0.05 mm Hg) for 18 hours. This gives 97% of a pure product of Rf=0.18 (A) and melting point=96°-7° C.

(3)

N₁-(2-methoxyethyl)-N-(adamantan-1-yl)-(L)-pyroglutamide 9.35 g (50 mmol) of the previously obtained acid are added in portions to 72 g (0.6 mol) of thionyl chloride. The mixture is kept at 50° C. for 2 hours and evaporated, the residue is taken up several times with benzene, the mixture is evaporated, the residue is taken up in 50 ml of chloroform and the mixture is run into a suspension of 15.1 g (0.1 mol) of adamantanamine in 120 ml of chloroform and 3.95 g (50 mmol) of pyridine. The mixture is heated under reflux for 5 hours and then stirred at ordinary temperature for 15 hours, cooled and filtered and the filtrate is evaporated. The residue is treated in the usual manner (cf. Example II(4)). The product is purified by chromatography on a silica column using a chloroform/acetone mixture as the eluent. This gives 53% of a pure product; Rf=0.22 (A); Rf=0.10 (B); melting point=128°-9° C.

NMR spectrum in CDCl$_3$ solution relative to TMS: 6.15 ppm (s), broad, 1H, NH; 4.10 ppm (m), 1H, CHCONH; 3.3 to 3.7 ppm (m), 4H, N—CH$_2$—CH$_2$—O—; 3.4 ppm (s), 3H, OCH$_3$; 2.15 to 2.65 ppm (m), 4H, —CH$_2$—CH$_2$—, pyrrolidone; 1.75 and 2.05 ppm (2s), 15H, adamantane.

EXAMPLE XIII

N$_1$-[2-cyanoethyl]-N-[adamantan-1-yl]-(L)-pyroglutamide 10.92 g (60 mmol) of N-[2-cyanoethyl]-(L)-pyroglutamic acid are added in portions to 86 g (0.72 mmol) of thionyl chloride in 60 ml of chloroform. The mixture is kept under reflux of the chloroform for 2 hours and evaporated to dryness, the residue is taken up several times with benzene, the mixture is evaporated, the residue is taken up in 50 ml of chloroform and the mixture is run into a suspension of 18.15 g (120 mmol) of adamantanamine in 250 ml of chloroform and 4.9 g (60 mmol) of pyridine. The mixture is heated under reflux for 4 hours and stirred at ordinary temperature overnight, cooled and filtered and the filtrate is evaporated. The residue is treated in the usual manner (cf. Example II(4)); the crude product is purified by recrystallization from the minimum quantity of isopropyl alcohol. This gives 30% of a pure product of Rf=0.24 (A), Rf=0.14 (B) and melting point=170°-2° C.

NMR spectrum is CDCl$_3$ solution relative to TMS: 6.20 ppm (s), 1H, NH; 4.15 ppm (m), 1H, CHCONH; 3.75 ppm (m), 2H, N—CH$_2$—CH$_2$—; 3.30 ppm (m), 2H, —CH$_2$—CH$_2$—CN; 2.40 to 2.85 ppm (m), 4H, —CH$_2$—CH$_2$, pyrrolidone; 1.70 and 2.0 ppm (2s), 15H, adamantane.

The derivatives according to the invention can be converted to pharmacologically acceptable salts by the usual techniques.

The antiviral properties of the derivatives can be demonstrated by the known techniques. Thus, by intraperitoneal or oral administration of the derivatives according to the invention to mice at doses of between 2 and 40 mg/kg of body weight, repeated every 6 hours and started 30 minutes before experimental infection with intranasal influenzae A.Z., an excellent antiviral activity is observed. For average levels of infection, protection is shown by an increase in the number of animals surviving and a lengthening of the survival time. For infections at a high dose of nearly 20 times the LD$_{50}$, the number of animals surviving is not increased but a significant lengthening of the survival time is observed. The best results are obtained if the products are administered more than four hours before experimental infection, which demonstrates the value of a prophylactic use for such compounds against viral infections of the influenzae type.

The derivatives according to the invention also prove to be hypocholesterolemic and hypobetalipoproteinemic.

Their administration to hypocholesterolemic rats at doses of between 0.1 and 0.7 mmol/kg causes a drop of about 20% in the serum cholesterol concentration and a reduction in the value of the ratio H.P.L. ("Heparin Precipitating Lipoproteins")/cholesterol to an average value of 0.91.

Furthermore, the derivatives according to the invention possess anticonvulsant properties; they delay the attack of convulsion induced by curare and are antianoxic in the confinement test at doses of the order of 100 mg/kg, administered orally. They also show a good anticataleptic activity at these same doses.

The derivatives according to the general formula (I) are preferably administered orally, but, as required, they can be administered by the other methods: parenterally, subcutaneously, intravenously, intramuscularly, intraperitoneally or transcutaneously.

This administration can also be combined with pharmaceutically acceptable excipients or diluents.

What is claimed is:

1. An N-(adamantan-1-yl)pyrrolidin-5-one-2-carboxamide derivative corresponding to the formula I:

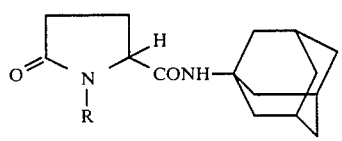

in which: R represents hydrogen, a lower alkyl radical containing from 1 to 7 carbon atoms, a lower alkyl radical containing from 1 to 7 carbon atoms substituted by an alkoxy group, a thioalkyl group or nitrile group, or an acyl radical of the type:

in which R$_1$ represents:

a lower alkyl radical containing from 1 to 7 carbon atoms, a 5 to 7 carbon atoms cycloalkyl ring having a—(CH$_2$)$_n$— radical attached thereto, wherein n=0,1 or 2, or a phenyl or benzyl radical, or a phenyl or benzyl radical substituted by 1-2 nitro, C$_1$ to C$_3$ alkyl, C$_1$ to C$_3$ alkoxy or halogen groups.

2. A compound as claimed in claim 1, wherein the pyrrolidonecarboxamide radical has the DL configuration.

3. A compound as claimed in claim 1, wherein the pyrrolidonecarboxamide radical has the L configuration.

4. A compound as claimed in claim 1 in which R represents the 3,4-dimethoxybenzoyl radical.

5. A compound as claimed in claim 1, wherein R=H.

6. A compound as claimed in claim 1 in which R represents the 4-methoxybenzoyl radical.

7. A compound as claimed in claim 1 in which R represents the 3,4-dimethoxyphenylacetyl radical.

8. A compound as claimed in claim 1 in which R represents the cyclopentylpropionyl radical.

9. A compound as claimed in claim 1 in which R represents the 2-propylpentanoyl radical.

10. A compound as claimed in claim 1 in which R represents the 2-ethylhexanoyl radical.

11. A compound as claimed in claim 1 in which R represents the hexanoyl radical.

12. An immunostimulant comprising an immunostimulating amount of at least one compound as claimed in claim 1 in a pharmaceutically acceptable diluent.

* * * * *